(12) United States Patent  
Scatterday

(10) Patent No.: US 8,539,959 B1  
(45) Date of Patent: Sep. 24, 2013

(54) ELECTRONIC CIGARETTE CONFIGURED TO SIMULATE THE NATURAL BURN OF A TRADITIONAL CIGARETTE

(71) Applicant: NJOY, Inc., Scottsdale, AZ (US)

(72) Inventor: Mark Scatterday, Scottsdale, AZ (US)

(73) Assignee: NJOY, Inc., Scottsdale, AZ (US)

( * ) Notice: Subject to any disclaimer, the term of this patent is extended or adjusted under 35 U.S.C. 154(b) by 0 days.

(21) Appl. No.: 13/729,396

(22) Filed: Dec. 28, 2012

Related U.S. Application Data

(63) Continuation of application No. 13/627,715, filed on Sep. 26, 2012.

(60) Provisional application No. 61/614,973, filed on Mar. 23, 2012, provisional application No. 61/674,712, filed on Jul. 23, 2012.

(51) Int. Cl.  
*A24B 1/04* (2006.01)

(52) U.S. Cl.  
USPC ............ 131/361; 131/194; 131/360; 131/329

(58) Field of Classification Search  
USPC .................................. 131/329, 194, 360, 361  
See application file for complete search history.

(56) References Cited

U.S. PATENT DOCUMENTS

| | | | |
|---|---|---|---|
| 4,771,796 A * | 9/1988 | Myer | 131/273 |
| 2006/0150991 A1 | 7/2006 | Lee | |
| 2010/0242974 A1 | 9/2010 | Pan | |
| 2011/0232654 A1 | 9/2011 | Mass | |
| 2012/0204889 A1 * | 8/2012 | Xiu | 131/273 |

* cited by examiner

*Primary Examiner* — Richard Crispino  
*Assistant Examiner* — Dionne Walls Mayes  
(74) *Attorney, Agent, or Firm* — Bookoff McAndrews, PLLC

(57) ABSTRACT

The present disclosure generally relates to electronic cigarette components. As will be disclosed, an electronic cigarette may have a translucent conduit and light chamber which, together, allow light from the light source to be diffused therethrough in such a way that the light emitted during inhalation simulates the natural burn of a traditional tobacco cigarette during inhalation. The electronic cigarette may also have a translucent ash simulator to further simulate the natural burn of a traditional tobacco cigarette during inhalation.

6 Claims, 4 Drawing Sheets

ELECTRONIC CIGARETTE CONFIGURED TO SIMULATE THE NATURAL BURN OF A TRADITIONAL CIGARETTE

CROSS-REFERENCE TO RELATED APPLICATIONS

This application is a continuation of U.S. application Ser. No. 13/627,715 titled ELECTRONIC CIGARETTE CONFIGURED TO SIMULATE THE NATURAL BURN OF A TRADITIONAL CIGARETTE that was filed on Sep. 26, 2012 in the name of Mark Scatterday and claims priority thereto. This application also claims priority to U.S. Provisional Application Ser. No. 61/614,973, titled ELECTRONIC CIGARETTE ATTACHMENTS, COMPONENTS AND HOLDERS to Craig Weiss and Mark Scatterday that was filed on Mar. 23, 2012 and to U.S. Provisional Application Ser. No. 61/674,712 titled ELECTRONIC CIGARETTE CONFIGURED TO SIMULATE THE NATURAL BURN OF A TRADITIONAL CIGARETTE to Mark Scatterday that was filed on Jul. 23, 2012.

TECHNICAL FIELD

This disclosure generally relates to alternative smoking devices, and more particularly, to an electronic cigarette configured to simulate the natural burn of a traditional cigarette.

SUMMARY

This summary is provided to introduce a selection of concepts in a simplified form that are further described below in the DESCRIPTION OF THE DISCLOSURE. This summary is not intended to identify key features of the claimed subject matter, nor is it intended to be used as an aid in determining the scope of the claimed subject matter.

In accordance with aspects of the present disclosure, electronic cigarette components are presented. The disclosure presents an electronic cigarette configured to simulate the natural burn of a traditional cigarette.

In accordance with one embodiment of the present invention, an electronic cigarette is disclosed. The electronic cigarette comprises a conduit adapted to contain internal components of an electronic cigarette device and a light chamber at a distal end of the conduit.

In accordance with another embodiment of the present invention, an electronic cigarette is disclosed. The electronic cigarette comprises a translucent conduit; internal components housed within the conduit, the internal components comprising: a unit containing liquid; a vaporizing unit for vaporizing the liquid within the unit containing liquid; a power source; an integrated circuit positioned within a distal end of the conduit; a light source coupled to the integrated circuit; an end piece coupled to the distal end of the conduit; and a light chamber within the conduit, the light chamber defined by the internal components at one end and by the end piece at another end; wherein the light chamber is illuminated when the electronic cigarette is inhaled and the light source is activated.

In accordance with another embodiment of the present invention, an electronic cigarette is disclosed. The electronic cigarette comprises: translucent conduit; internal components housed within the conduit, the internal components comprising: a unit containing liquid; a vaporizing unit for vaporizing the liquid within the unit containing liquid; a power source; an integrated circuit positioned within a distal end of the conduit; a light source coupled to the integrated circuit; a translucent ash simulator coupled to the distal end of the conduit; a light chamber within the conduit, the light chamber defined by the internal components at one end and by the end piece at another end; and a translucent housing comprising: a shaft portion inserted into the distal end of the conduit, the shaft portion for receiving the integrated circuit; and an annular flange that abuts a distal edge of the conduit; wherein the light chamber is illuminated when the electronic cigarette is inhaled and the light source is activated.

BRIEF DESCRIPTION OF THE DRAWINGS

The novel features believed to be characteristic of the application are set forth in the appended claims. The novel features believed to be characteristic of the application are set forth in the appended claims. In the descriptions that follow, like parts are marked throughout the specification and drawings with the same numerals, respectively. The drawing figures are not necessarily drawn to scale and certain figures can be shown in exaggerated or generalized form in the interest of clarity and conciseness. The application itself, however, as well as a preferred mode of use, further objectives and advantages thereof, will be best understood by reference to the following detailed description of illustrative embodiments when read in conjunction with the accompanying drawings, wherein:

DESCRIPTION OF THE DISCLOSURE

The description set forth below is intended as a description of presently preferred embodiments of the disclosure and is not intended to represent the only forms in which the present disclosure can be constructed and/or utilized. The description sets forth the functions and the sequence of steps for constructing and operating the disclosure. It is to be understood, however, that the same or equivalent functions and sequences can be accomplished by different embodiments that are also intended to be encompassed within the spirit and scope of this disclosure.

The present disclosure generally relates to electronic cigarettes. As will be disclosed, an electronic cigarette can have a translucent conduit for protecting its internal components and light chamber for diffusing light during inhalation of the electronic cigarette. A number of advantages can be provided by the electronic cigarette components described herein. The translucent conduit and the light chamber of the electronic cigarette may simulate the diffused light of the natural burn of a traditional cigarette. A number of additional advantages will become apparent from the description provided below.

Prior art alternative smoking devices can include a number of components consisting of a power source such as a battery, vaporizing unit, and a unit containing liquid that contains nicotine. The battery can be a pre-charged, disposable type of device that is not rechargeable or, alternatively, a rechargeable battery. In one embodiment the unit containing liquid may be cotton or some other suitable absorptive fiber that is saturated with liquid, wherein the unit containing liquid surrounds the vaporizing unit within the conduit. The vaporizing unit may then comprise a heating element wrapped about a wick, wherein the wick absorbs liquid from the surrounding unit containing liquid. Upon inhalation, negative pressure causes a sensor to turn on the heating element, which then causes the liquid absorbed by the wick to vaporize and exit the electronic cigarette through an air tube. When used, the tip of the device can light up simulating the effects of a traditional cigarette. It should be clearly understood that substantial benefit may be derived from the use of alternative configurations of the internal components.

The body of traditional electronic cigarette embodiments can have a conduit that is made of metal. The metal in the device allows for sturdiness as well as protects the interior components. The metal of the device, however, can lead to drawbacks. These drawbacks can include a completely opaque conduit that does not allow any light to pass through it, resulting in an unrealistic simulation of the burn of a traditional cigarette when it is inhaled.

Figure 1:
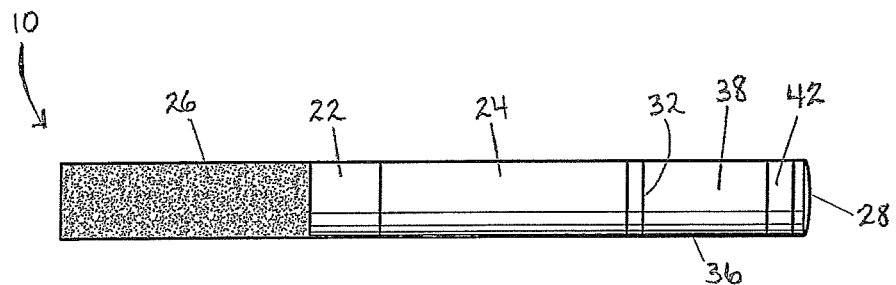
FIG. 1 is a cross-sectional side view of an electronic cigarette in accordance with one or more embodiments of the present invention.
Figure 2:
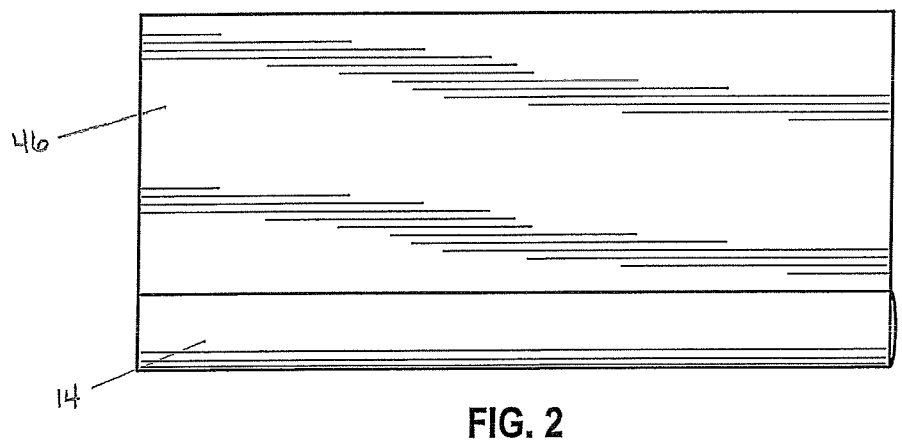
FIG. 2 is a side view of wrapper being coupled to a conduit of an electronic cigarette in accordance with one or more embodiments of the present invention.

FIGS. 1 through 9, show an electronic cigarette 10 in accordance with one or more embodiments of the present invention. In the present invention, the metal conduit is replaced with one that is, at least in part, translucent. It should also be clearly understood that substantial benefit may be derived from the entire conduit 14 being translucent. The conduit 14 may be made of plastic, polyvinyl chloride (PVC), polyethylene, polypropylene, polycarbonate, or other suitable material that is more translucent than the metal used within the prior art alternative smoking devices. As shown in FIG. 2, the conduit 14 can extend the entire length of the electronic cigarette 10 and the conduit 14 may be covered with a wrapper 46 constructed of paper or another suitable material. As shown in FIG. 1, the conduit 14 can cover the components of the electronic cigarette 10 which may include: a vaporizing unit 22, battery 24, unit containing liquid 26, integrated circuit 32, light source 34 (see FIG. 4), light chamber 36, and end piece 28. The conduit 14 can also cover a portion or the entirety of the filter 12 (see FIG. 9). With this embodiment, light from the light source 34 may be diffused through at least a portion of the length of the conduit 14 moving from the tip of the electronic cigarette 10 toward a user's mouth, in such a way that the light emitted during inhalation simulates the natural burning down of a traditional tobacco cigarette during inhalation.

In one embodiment, the internal components of the electronic cigarette 10 (e.g. the vaporizing unit 22, battery 24, unit containing liquid 26, integrated circuit 32, and light source 34) are positioned within the conduit 14 to leave a space within the conduit 14 at the distal end 18, thereby creating a light chamber 36. In one embodiment, the light source 34, which may be an LED or other suitable light source, is coupled to the integrated circuit 32, either directly or with wires 48 (see FIG. 4) and faces outwardly toward the distal end 18 of the electronic cigarette 10. The light source 34 may be positioned a suitable distance from the end piece 28 of the electronic cigarette 10, thereby creating the light chamber 36 within the conduit 14 at the distal end 18 of the electronic cigarette 10. It should be clearly understood that the light source 34 may also be positioned in an alternative configuration within the conduit 14, as long as a space is left within the conduit 14 for creation of the light chamber 36. It should also be clearly understood that the light chamber 16 may extend any desired distance from the distal end 18 of the electronic cigarette 10 toward the proximal end 16 of the electronic cigarette 10.

When the user inhales the electronic cigarette 10, the light source 34 illuminates and the emitted light shines within the light chamber 36 and is diffused through the translucent conduit 14 at the distal end 18 of the electronic cigarette 10. The light will have little or no diffusion through the portions of the translucent conduit 14 that contain the other internal components, such as the vaporizing unit 22, battery 24, and unit containing liquid 26. Much like the natural burn of a traditional cigarette during inhalation, the emitted light is therefore visible through the end piece 28 as well as through the light chamber 36 within the conduit 14 at the distal end 18 of the electronic cigarette 10. The light source 34 may emit light at different levels of intensity, which may vary depending upon the speed and/or force at which the user inhales the electronic cigarette 10. The light emitted from the light source 34 may also gradually brighten while the electronic cigarette 10 is being inhaled and may then also fade to dim or dark after the electronic cigarette 10 is inhaled. The light source 34 may also emit a continuous glow when the electronic cigarette 10 is not being inhaled, so as to simulate the continuous glow of a lit traditional cigarette when it is not being inhaled. Through this embodiment, the user will be able to see the light emitted from the distal end 18 of the electronic cigarette 10 during inhalation and, as well, will experience the sensation that the electronic cigarette 10 is burning down in the manner of a traditional cigarette.

Figure 3:
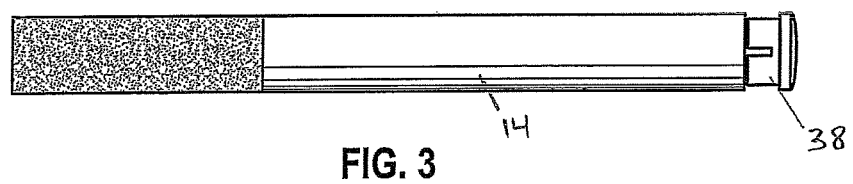
FIG. 3 is a side view of an electronic cigarette in accordance with one or more embodiments of the present invention.
Figure 4:
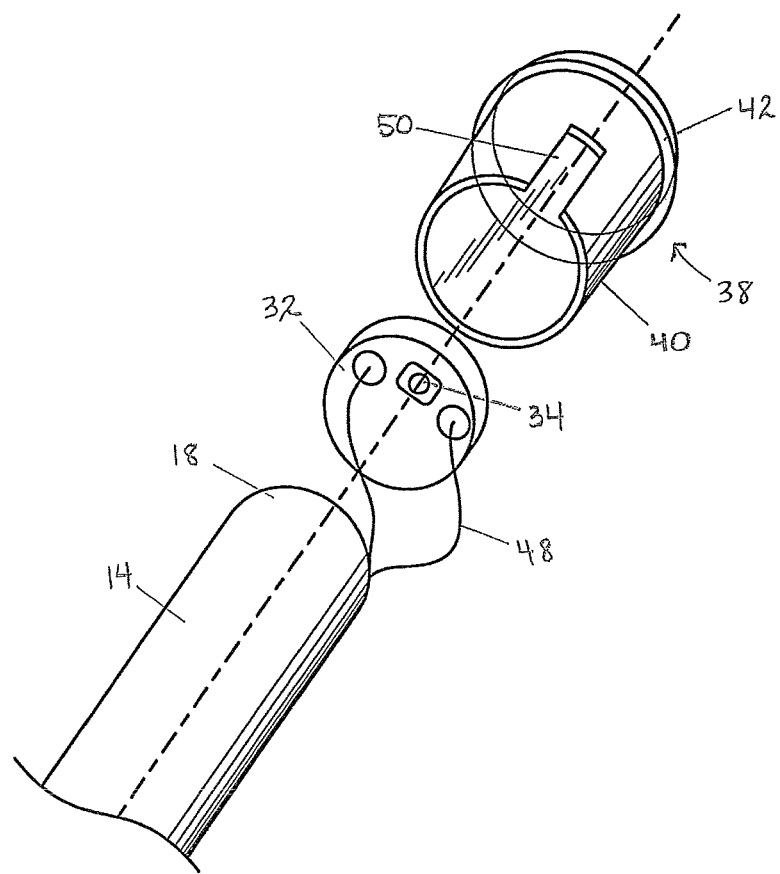
FIG. 4 is an exploded perspective view of a conduit, integrated circuit, and housing of an electronic cigarette in accordance with one or more embodiments of the present invention.
Figure 5:
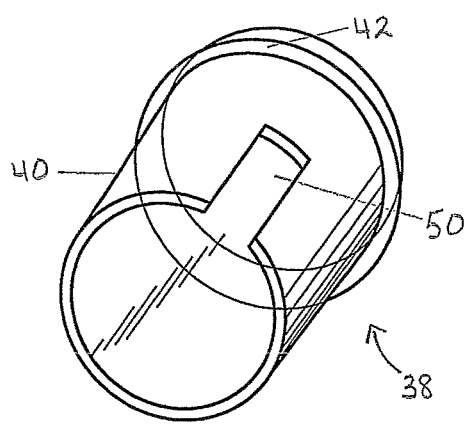
FIG. 5 is a perspective view of a housing used with an electronic cigarette in accordance with one or more embodiments of the present invention.
Figure 6:
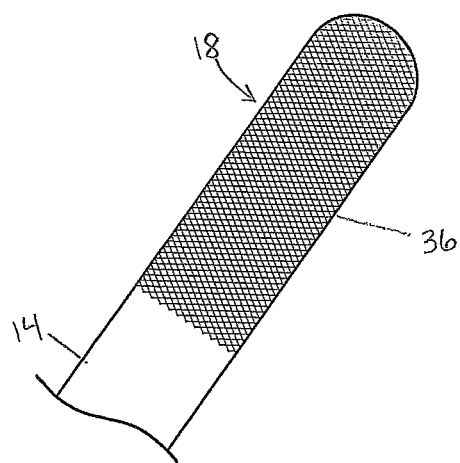
FIG. 6 perspective view of a distal end of an electronic cigarette in accordance with one or more embodiments of the present invention, showing the light chamber simulating the burn of a traditional cigarette when inhaled.
Figure 7:
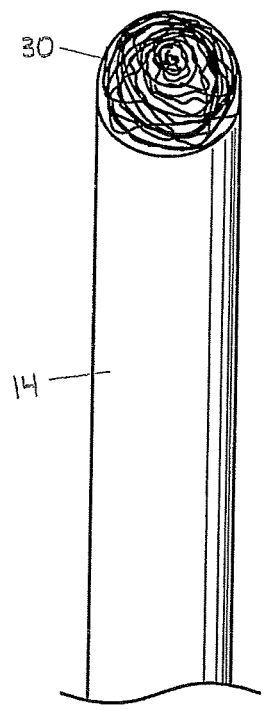
FIG. 7 is a perspective view of an ash simulator coupled to a distal end of an electronic cigarette in accordance with one or more embodiments of the present invention.
Figure 8:
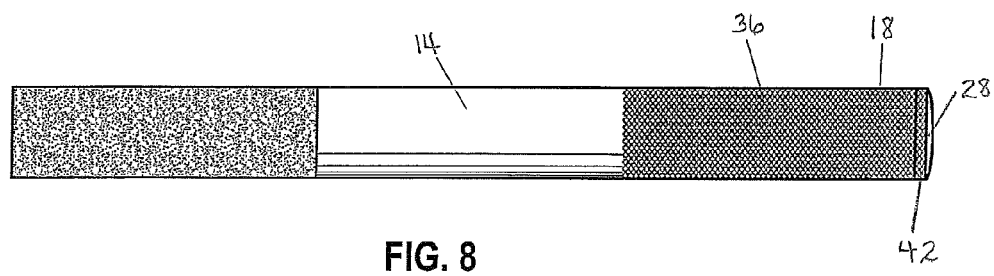
FIG. 8 is a side view of an electronic cigarette in accordance with one or more embodiments of the present invention, showing the light chamber simulating the burn of a traditional cigarette when inhaled.
Figure 9:
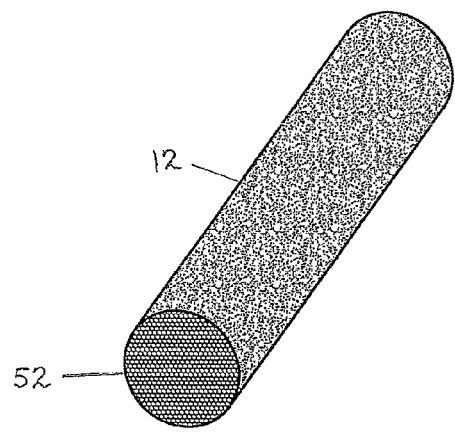
FIG. 9 a porous membrane filter of an electronic cigarette in accordance with one or more embodiments of the present invention.

Referring to FIGS. 3-5, in another embodiment, the electronic cigarette 10 further comprises a housing 38 that may be inserted into the distal end 18 of the conduit 14. The housing 38 may be cylindrical and have an outside diameter smaller than the inside diameter of the conduit 14 so that a proximal end (or shaft 40) of the housing 38 may be inserted into and frictionally engage the inside surface of the conduit 14 at the distal end 18 of the electronic cigarette 10. The shaft 40 of the housing 38 may have an inside diameter larger than the outside diameter of the integrated circuit 32 so that the integrated circuit 32 may be held securely within the shaft 40 of the housing 38 and so that light may be diffused around the integrated circuit 32 and through the portion of the shaft 40 of the housing 38 that surrounds the integrated circuit 32. The shaft 40 of the housing 38 may also define a notch 50 to accommodate for any wires 48 coupling the integrated circuit 32 to the battery 24. By positioning the wires 48 within the notch 50, the housing 38 and the wires 48 may rest flush against the inner surface of the conduit 14 at the distal end 18 of the electronic cigarette 10 when the shaft 40 of the housing 38 is inserted into the conduit 14. The end piece 28 of the electronic cigarette 10 may also be coupled to a distal end 18 of the housing 38. The housing 38 may also have an annular flange 42 that has the same outside diameter as the outside diameter of the conduit 14, so that when the shaft 40 of the housing 38 is inserted into the conduit 14, the annular flange 42 abuts the distal edge 20 of the conduit 14, allowing for a smooth continuous surface from the filter 12, through the length of the conduit 14, and the housing 38, and finally to the end piece 28. At least a portion of the housing 38 may be made of clear plastic or of some other suitable translucent material so that the light may diffuse through it as well as through the conduit 14. It should be clearly understood that substantial benefit may be derived from the entire housing 38 being translucent.

In one embodiment, the degree of translucency may be uniform throughout the conduit 14. In another embodiment, the light chamber 36 may have multiple areas of varying degrees of translucency. When the electronic cigarette 10 is inhaled, the light illuminates the light chamber 36 and these areas of varying degrees of translucency will help to simulate the uneven burn area that occurs in the tobacco of a traditional cigarette.

A filter 12 replicating that used in traditional cigarettes may be used with the present electronic cigarette 10. In previous configurations, the filter 12 has always had a hole for allowing smoke/vapor to pass therethrough. The filter 12 of the present invention may be fully enclosed. A porous membrane 52, porous molded disc, acidic fiber, or the like may be used to allow enough of the vapor to pass through simulating the amount of sucking required by the user to mimic a traditional cigarette filter.

The end piece 28 of the electronic cigarette 10 of the present invention may be an ash simulator 30. Typically, the ash simulators 30 may replicate burnt tobacco or other material used in smoking implements. The ash simulators 30 may be translucent so that light may diffuse through the ash simulator 30 when the electronic cigarette 10 is inhaled. When the electronic cigarette 10 is inhaled, light from the light source 34 will diffuse through the light chamber 36 of the conduit 14 and the ash simulator 30 (and the shaft 40 and annular flange 42 of the housing 38 if one is present) to simulate the natural burn of a traditional cigarette when inhaled.

The foregoing description is provided to enable any person skilled in the relevant art to practice the various embodiments described herein. Various modifications to these embodiments will be readily apparent to those skilled in the relevant art, and generic principles defined herein can be applied to other embodiments. Thus, the claims are not intended to be limited to the embodiments shown and described herein, but are to be accorded the full scope consistent with the language of the claims, wherein reference to an element in the singular is not intended to mean "one and only one" unless specifically stated, but rather "one or more." All structural and functional equivalents to the elements of the various embodiments described throughout this disclosure that are known or later come to be known to those of ordinary skill in the relevant art are expressly incorporated herein by reference and intended to be encompassed by the claims. Moreover, nothing disclosed herein is intended to be dedicated to the public.

I claim:

1. An electronic cigarette comprising:
    a conduit adapted to contain internal components of an electronic cigarette device;
    a light chamber at a distal end of the conduit, wherein at least a portion of the distal end of the conduit is translucent and wherein the light chamber is a space within the distal end of the conduit defined by the internal components within the conduit at one end and by an end piece coupled to a distal edge of the conduit at another end;
    an integrated circuit positioned within the distal end of the conduit;
    a light source coupled to the integrated circuit; and
    a housing for securing the integrated circuit within the distal end of the conduit, wherein at least a portion of the housing is translucent and wherein the housing comprises:
        a shaft portion for insertion into the distal end of the conduit;
        an annular flange that abuts the distal edge of the conduit; and
        a notch defined by the shaft of the housing, the notch adapted to receive wires connected to the integrated circuit;
    wherein the light chamber is illuminated when the electronic cigarette is inhaled and the light source is activated.

2. An electronic cigarette comprising;
    a translucent conduit;
    internal components housed within the conduit, the internal components comprising:
        a unit containing liquid;
        a vaporizing unit for vaporizing the liquid within the unit containing liquid;
        a power source;
        an integrated circuit positioned within a distal end of the conduit;
        a light source coupled to the integrated circuit;
    an end piece coupled to the distal end of the conduit;
    a light chamber within the conduit, the light chamber defined by the internal components at one end and by the end piece at another end; and
    a translucent housing for receiving the integrated circuit and securing the integrated circuit within the distal end of the conduit wherein the housing comprises:
        a shaft portion for insertion into the distal end of the conduit;
        an annular flange that abuts a distal edge of the conduit; and
        a notch defined by the shaft of the housing, the notch adapted to receive wires connecting the integrated circuit to the power source;
    wherein the light chamber is illuminated when the electronic cigarette is inhaled and the light source is activated.

3. The electronic cigarette of claim 2 further comprising a porous membrane filter coupled to a proximal end of the conduit.

4. The electronic cigarette of claim 2 further comprising a translucent ash simulator coupled to the end piece.

5. The electronic cigarette of claim 2 wherein a translucency of the light chamber is uneven.

6. An electronic cigarette comprising:
    a translucent conduit;
    internal components housed within the conduit, the internal components comprising:
        a unit containing liquid;
        a vaporizing unit for vaporizing the liquid within the unit containing liquid;
        a power source;
        an integrated circuit positioned within a distal end of the conduit;
        a light source coupled to the integrated circuit;
    a translucent ash simulator coupled to the distal end of the conduit;

a light chamber within the conduit, the light chamber defined by the internal components at one end and by the end piece at another end; and a translucent housing comprising:
- a shaft portion inserted into the distal end of the conduit, the shaft portion for receiving the integrated circuit;
- an annular flange that abuts a distal edge of the conduit; and
- a notch defined by the shaft of the housing, the notch adapted to receive wires connected to the integrated circuit;

wherein the light chamber is illuminated when the electronic cigarette is inhaled and the light source is activated.

* * * * *